(12) United States Patent
McHugo et al.

(10) Patent No.: US 8,932,342 B2
(45) Date of Patent: Jan. 13, 2015

(54) CONTROLLED RELEASE AND RECAPTURE PROSTHETIC DEPLOYMENT DEVICE

(75) Inventors: Vincent McHugo, Tipperary (IE); Kenneth C. Kennedy, Clemmons, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 470 days.

(21) Appl. No.: 13/192,130

(22) Filed: Jul. 27, 2011

(65) Prior Publication Data

US 2012/0029607 A1 Feb. 2, 2012

Related U.S. Application Data

(60) Provisional application No. 61/369,183, filed on Jul. 30, 2010.

(51) Int. Cl.
*A61F 2/06* (2013.01)
*A61F 2/95* (2013.01)
*A61F 2/966* (2013.01)

(52) U.S. Cl.
CPC . *A61F 2/95* (2013.01); *A61F 2/966* (2013.01); *A61F 2002/9517* (2013.01); *A61F 2002/9534* (2013.01)
USPC ............ 623/1.11; 623/1.2; 606/194; 606/198

(58) Field of Classification Search
CPC ... A61F 2/95; A61F 2/966; A61F 2002/9517; A61F 2002/9534
USPC ............................ 623/1.11, 1.2; 606/194, 198
See application file for complete search history.

(56) References Cited

U.S. PATENT DOCUMENTS

| 1,724,983 | A | | 8/1929 | Weiss |
| 3,132,549 | A | | 5/1964 | Lee |
| 3,888,258 | A | | 6/1975 | Akiyama |
| 3,897,786 | A | | 8/1975 | Garnett et al. |
| 4,559,041 | A | | 12/1985 | Razi |
| 4,921,484 | A | | 5/1990 | Hillstead |
| 5,275,151 | A | | 1/1994 | Shockey et al. |
| 5,415,664 | A | * | 5/1995 | Pinchuk ...................... 623/1.11 |

(Continued)

FOREIGN PATENT DOCUMENTS

| EP | 0747021 A2 | 12/1996 |
| WO | WO 95/23008 A1 | 8/1995 |

(Continued)

OTHER PUBLICATIONS

International Search Report for International Application No. PCT/US2009/069721, dated Feb. 19, 2010, pages.

(Continued)

*Primary Examiner* — Tuan V Nguyen
*Assistant Examiner* — Tin Nguyen
(74) *Attorney, Agent, or Firm* — Brinks Gilson & Lione

(57) ABSTRACT

A delivery device for deploying and resheathing an expandable prosthesis and method of use thereof are described. The delivery device includes a fixed outer sheath and a pusher member that is configured for retracting in a proximal direction and resheathing the prosthesis. The device includes two plates engaging the pusher member, with a first plate configured engage the pusher member to prevent proximal movement and the other plate configured to engage the pusher member for distal movement.

18 Claims, 4 Drawing Sheets

(56) References Cited

U.S. PATENT DOCUMENTS

| | | | |
|---|---|---|---|
| 5,433,723 | A | 7/1995 | Lindenberg et al. |
| 5,443,477 | A | 8/1995 | Marin et al. |
| 5,458,615 | A | 10/1995 | Klemm et al. |
| 5,681,323 | A | 10/1997 | Arick |
| 5,683,451 | A | 11/1997 | Lenker et al. |
| 5,690,644 | A | 11/1997 | Yurek et al. |
| 5,700,269 | A | 12/1997 | Pinchuk et al. |
| 5,702,418 | A | 12/1997 | Ravenscroft |
| 5,709,703 | A | 1/1998 | Lukic et al. |
| 5,733,325 | A | 3/1998 | Robinson et al. |
| 5,759,186 | A | 6/1998 | Bachmann et al. |
| 5,776,142 | A | 7/1998 | Gunderson |
| 5,833,694 | A | 11/1998 | Poncet |
| 5,906,619 | A | 5/1999 | Olson et al. |
| 5,944,727 | A | 8/1999 | Ahari et al. |
| 5,968,052 | A | 10/1999 | Sullivan, III et al. |
| 5,993,460 | A | 11/1999 | Beitelia et al. |
| 6,093,194 | A | 7/2000 | Mikus et al. |
| 6,146,415 | A | 11/2000 | Fitz |
| 6,162,231 | A | 12/2000 | Mikus et al. |
| 6,168,610 | B1 | 1/2001 | Marin et al. |
| 6,238,402 | B1 | 5/2001 | Sullivan, III et al. |
| 6,254,628 | B1 * | 7/2001 | Wallace et al. ............ 623/1.12 |
| 6,346,118 | B1 | 2/2002 | Baker et al. |
| 6,375,676 | B1 | 4/2002 | Cox |
| 6,383,211 | B1 | 5/2002 | Stachle |
| 6,391,050 | B1 | 5/2002 | Broome |
| 6,391,051 | B2 | 5/2002 | Sullivan, III et al. |
| 6,402,760 | B1 | 6/2002 | Fedida |
| 6,413,269 | B1 | 7/2002 | Bui et al. |
| 6,428,566 | B1 | 8/2002 | Holt |
| 6,514,261 | B1 | 2/2003 | Randall et al. |
| 6,520,983 | B1 | 2/2003 | Colgan et al. |
| 6,592,549 | B2 | 7/2003 | Gerdts et al. |
| 6,599,296 | B1 | 7/2003 | Gillick et al. |
| 6,629,981 | B2 | 10/2003 | Bui et al. |
| 6,669,719 | B2 | 12/2003 | Wallace et al. |
| 6,673,101 | B1 | 1/2004 | Fitzgerald et al. |
| 6,695,862 | B2 | 2/2004 | Cox et al. |
| 6,749,627 | B2 | 6/2004 | Thompson et al. |
| 6,755,854 | B2 | 6/2004 | Gillick et al. |
| 6,755,855 | B2 | 6/2004 | Yurek et al. |
| 6,786,918 | B1 | 9/2004 | Krivoruchko et al. |
| 6,808,529 | B2 | 10/2004 | Fulkerson |
| 6,860,898 | B2 | 3/2005 | Stack et al. |
| 6,866,669 | B2 | 3/2005 | Buzzard et al. |
| 6,890,317 | B2 | 5/2005 | Gerdts et al. |
| 6,893,458 | B2 | 5/2005 | Cox et al. |
| 6,911,039 | B2 | 6/2005 | Shiu et al. |
| 6,926,732 | B2 | 8/2005 | Derus et al. |
| 6,939,352 | B2 | 9/2005 | Buzzard et al. |
| 6,942,688 | B2 | 9/2005 | Bartholf et al. |
| 6,991,646 | B2 | 1/2006 | Clerc et al. |
| 2002/0007206 | A1 | 1/2002 | Bui et al. |
| 2002/0095203 | A1 | 7/2002 | Thompson et al. |
| 2003/0093084 | A1 | 5/2003 | Nissan et al. |
| 2003/0144671 | A1 | 7/2003 | Brooks et al. |
| 2003/0225445 | A1 | 12/2003 | Derus et al. |
| 2004/0006380 | A1 | 1/2004 | Buck et al. |
| 2004/0010265 | A1 | 1/2004 | Karpiel |
| 2004/0093057 | A1 | 5/2004 | Bolduc et al. |
| 2004/0181239 | A1 | 9/2004 | Dorn et al. |
| 2004/0186547 | A1 | 9/2004 | Dorn et al. |
| 2004/0193180 | A1 | 9/2004 | Buzzard et al. |
| 2004/0215229 | A1 | 10/2004 | Coyle |
| 2004/0220653 | A1 | 11/2004 | Borg et al. |
| 2004/0267282 | A1 | 12/2004 | Shkarubo et al. |
| 2005/0021123 | A1 | 1/2005 | Dorn et al. |
| 2005/0033402 | A1 | 2/2005 | Cully et al. |
| 2005/0033403 | A1 | 2/2005 | Ward et al. |
| 2005/0060016 | A1 | 3/2005 | Wu et al. |
| 2005/0080476 | A1 | 4/2005 | Gunderson et al. |
| 2005/0090834 | A1 | 4/2005 | Chiang et al. |
| 2005/0090890 | A1 | 4/2005 | Wu et al. |
| 2005/0113902 | A1 | 5/2005 | Geiser et al. |
| 2005/0131514 | A1 | 6/2005 | Hijlkema et al. |
| 2005/0149159 | A1 | 7/2005 | Andreas et al. |
| 2005/0177246 | A1 | 8/2005 | Datta et al. |
| 2005/0182475 | A1 | 8/2005 | Jen et al. |
| 2005/0209670 | A1 | 9/2005 | George et al. |
| 2005/0209685 | A1 | 9/2005 | Shifrin et al. |
| 2005/0240254 | A1 | 10/2005 | Austin |
| 2005/0256562 | A1 | 11/2005 | Clerc et al. |
| 2005/0273151 | A1 | 12/2005 | Fulkerson et al. |
| 2005/0288763 | A1 | 12/2005 | Andreas et al. |
| 2005/0288764 | A1 | 12/2005 | Snow et al. |
| 2005/0288766 | A1 | 12/2005 | Plain et al. |
| 2006/0009858 | A1 | 1/2006 | Levine et al. |
| 2006/0184224 | A1 | 8/2006 | Angel |
| 2010/0168834 | A1 | 7/2010 | Ryan et al. |

FOREIGN PATENT DOCUMENTS

| | | |
|---|---|---|
| WO | WO 02/05885 A2 | 1/2002 |
| WO | WO 2005/115254 A2 | 12/2005 |
| WO | WO 2007/005799 A1 | 1/2007 |
| WO | WO 2007/022395 A1 | 2/2007 |
| WO | WO 2008/042266 A2 | 4/2008 |
| WO | WO 2009/012061 A1 | 1/2009 |

OTHER PUBLICATIONS

Written Opinion of the International Searching Authority for International Application No. PCT/US2009/069721, dated Feb. 19, 2010, pages.

International Search Report for International Application No. PCT/US2011/045282, dated Oct. 28, 2011, 3 pages.

Written Opinion of the International Searching Authority for International Application No. PCT/US2011/045282, dated Oct. 28, 2011, 7 pages.

\* cited by examiner

CONTROLLED RELEASE AND RECAPTURE PROSTHETIC DEPLOYMENT DEVICE

CROSS-REFERENCE TO RELATED APPLICATIONS

This application is a non-provisional application which claims priority to U.S. provisional application Ser. No. 61/369,183, filed Jun. 30, 2010, which is incorporated by reference herein in its entirety.

TECHNICAL FIELD

This invention relates to a medical device and, in particular to a delivery device for a self-expanding prosthesis and a method of delivering and deploying the prosthesis into a body lumen.

BACKGROUND

A self-expanding prosthesis such as a stent may be introduced into a patient's body using a delivery device that includes a push-pull mechanism with an outer catheter coaxially slidably disposed over an inner catheter. The prosthesis is disposed in a circumferentially-restrained configuration at the distal end of the device between the inner catheter and the outer catheter. The prosthesis may be deployed by proximally pulling back the outer catheter relative to the inner catheter, exposing the prosthesis and allowing it to deploy/circumferentially expand.

The push-pull delivery device described above may have several shortcomings. For example, when using this conventional push-pull delivery device, a physician may inadvertently retract the outer catheter too far and prematurely deploy the prosthesis in an incorrect position within a body lumen. In that circumstance, repositioning the prosthesis may be difficult, if not impossible, because the prosthesis already will have radially self-expanded and engaged the body lumen.

Accordingly, there is a need for a delivery system that can increase the control, accuracy and ease of placement during deployment of a prosthesis. The embodiments described below may be useful for increasing the control, accuracy and ease of placement during deployment of the prosthesis and may also solve other problems.

SUMMARY

Accordingly, a delivery device is provided including a fixed outer catheter sheath and a longitudinally-movable pusher member that is configured to retract/advance in proximal/distal directions for deploying and recapturing/resheathing an intraluminal prosthesis.

BRIEF DESCRIPTION OF THE DRAWINGS

Embodiments are described by way of example with reference to the accompanying drawings, in which.

DETAILED DESCRIPTION OF THE PREFERRED EMBODIMENTS

Figure 1A:
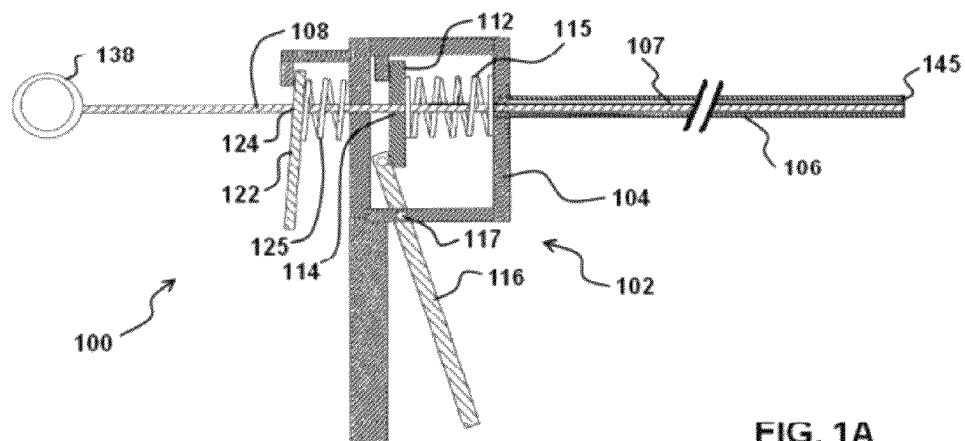
FIGS. 1A-1C show a partial section view of a delivery device embodiment and method of use.

The embodiments are described with reference to the drawings in which like elements are generally referred to by like numerals. The relationship and functioning of the various elements of the embodiments may be understood by reference to the drawings and the following detailed description. However, the embodiments described below are provided by way of example only, and the invention is not limited to the embodiments illustrated in the drawings. It should also be understood that the drawings are not to scale, and—in certain instances—details have been omitted that are not necessary for an understanding of the embodiments such as conventional details of fabrication and assembly.

Throughout the specification, the terms "distal" and "distally" shall denote a position, direction, or orientation that is generally away from the physician (including any other person holding/operating a device) and/or toward a treatment zone/patient. Accordingly, the terms "proximal" and "proximally" shall denote a position, direction, or orientation that is generally towards the physician. In FIGS. 1A-1C, 3A-3C, and 4A-4C, "distal" is generally to the right, and "proximal" is generally to the left. Various other constructions of deployment devices and methods may be understood with reference to U.S. patent application Ser. No. 12/649,046 to Ryan et al., filed Dec. 29, 2009, which is incorporated by reference herein in its entirety.

Referring now to the drawings in FIGS. 1A-4C, embodiments of a delivery device for deploying a self-expanding prosthesis are shown. As will be discussed, the delivery device is configured with the ability to resheath and reposition the prosthesis, thereby substantially increasing the control and accuracy of a deployment process as compared with conventional delivery devices.

Figure 1B:
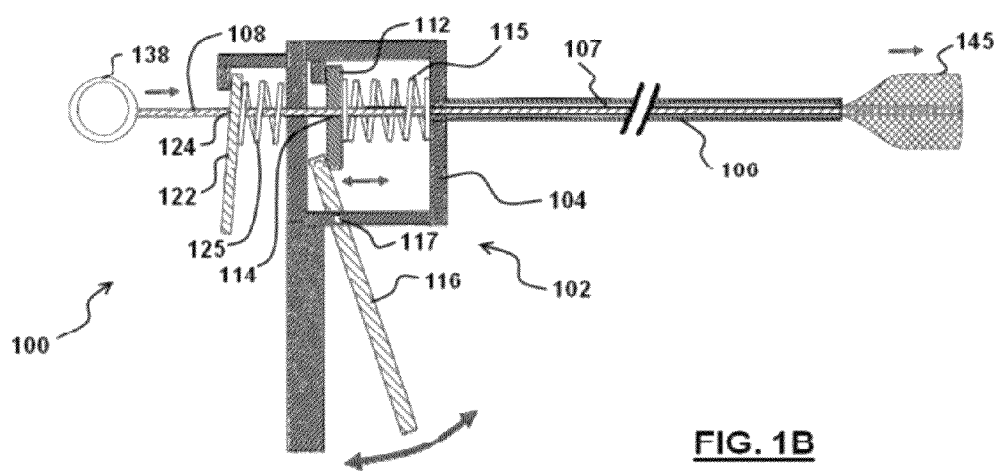
Figure 1C:
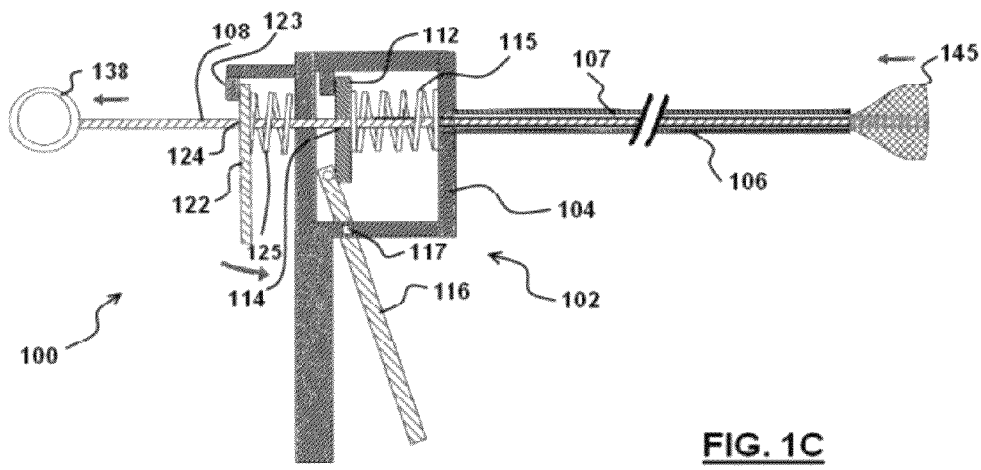

FIGS. 1A-1C show one embodiment of a delivery device 100, with reference to a method of use. The delivery device 100 includes a handle 102 with a handle body 104 and an elongate tubular sheath 106 fixedly attached to and extending distally from the handle body 104. An elongate pusher member 108 extends slidably through a longitudinal lumen 107 of the sheath 106. The handle body 104 is shown in a longitudinal cutaway view revealing the internal components of the handle 102.

The interior of the handle 102 includes an advancement plate member 112 that is biased toward the proximal end of the pusher member 108. In this embodiment, the advancement member 112 is shown as being biased by a coil spring 115, but other biasing means known in the art may be used. The advancement member 112 includes an advancement member aperture 114 through its thickness, through which the pusher member 108 extends. A trigger member 116 is pivotably mounted to the handle body 104 and is connected to or otherwise disposed in operative contact with the advancement member 112. When the pivot axis 117 is configured as shown, pivoting the lower portion of the trigger member 116 proximally toward the handle body 104 will pivot the upper portion of the trigger member 116 distally, pushing the advancement member 112 distally. When advanced distally by motivation from the trigger member 116, the advancement member 112 engages (in the manner described below with reference to FIGS. 2A-2B) and pushes distally the pusher member 108.

A keeper plate member 122 is also mounted to the handle body 104 and biased toward its proximal end against a keeper stop 123. In this embodiment, the keeper member 122 is shown as being biased by a coil spring 125, but other biasing means known in the art may be used. The keeper member 122 includes a keeper member aperture 124 through its thickness, through which the pusher member 108 extends. The keeper member functions as a "parking brake" or retaining means that will prevent proximal movement of the pusher member 108 when engaged thereto. This may be needed because, as a stent is deployed distally, the sheath 106 may stretch distally and then—when attempting to relax and return to its original length—it may introduce backlash that would drive the pusher 108 proximally if it weren't held in place.

The proximal end of the pusher member 108 may include a handle or other grasping portion such as a ring 138 that will facilitate a user grasping the pusher member 108 and moving it proximally and/or distally (albeit in a generally less controlled fashion than by employing the advancement and keeper/retractor members 112, 122). A distal portion of the pusher member 108 is attached to an expandable prosthesis such as, for example, an intraluminal device embodied as a self-expanding stent 145 (which, because it is sheathed in lumen 107 is not clearly visible in FIG. 1A). The stent 145 may be constrained by this attachment and/or by the sheath 106. In certain embodiments, the sheath and pusher member will be sufficiently flexible and elongate to introduce a prosthetic device into a patient's alimentary canal. For example, the device 100 may be used to introduce a stent into a patient's esophagus (e.g., via the patient's mouth) or along an intestinal lumen. Device embodiments may be used through natural and/or surgically-created orifices, and may be practiced on a scale suitable for vascular stenting.

Figure 2A:
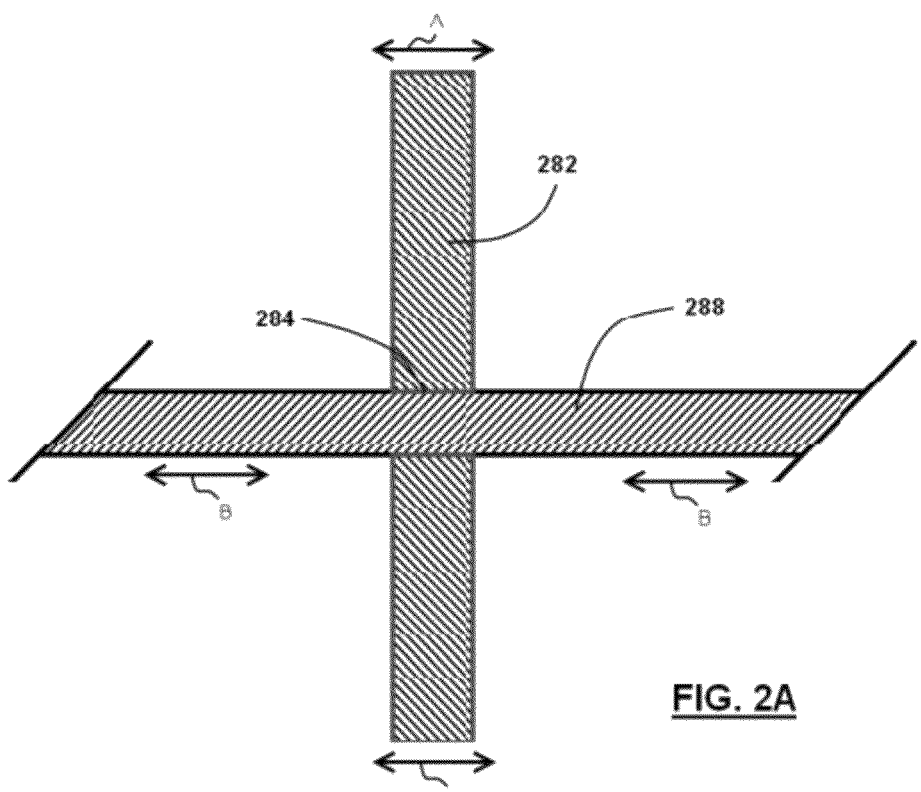
FIGS. 2A-2B show a diagrammatic section view of plate/pusher member interaction.
Figure 2B:
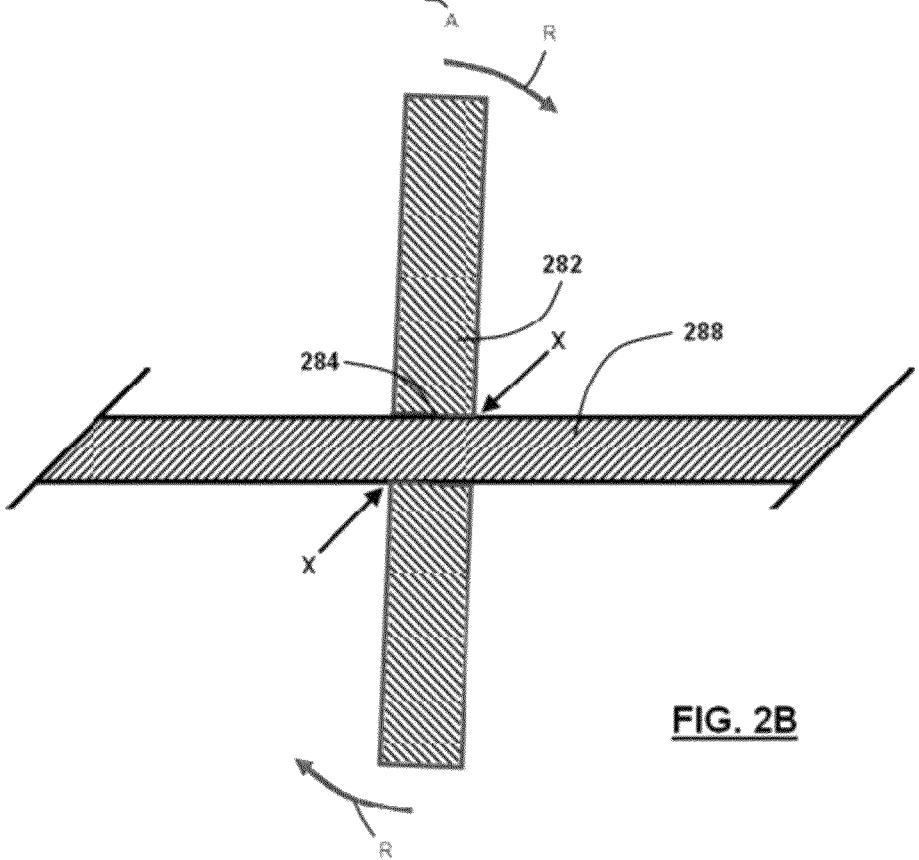

FIGS. 2A-2B illustrate the principle of operation of the attachment member 112 and the keeper member 122 with pusher member 108 (as well as analogous components of the other embodiments herein). The operation is described with reference to an apertured locking/gripping plate 282 (analogous to those members 112, 122, which function in the same manner) and a through-rod 288 (analogous to the pusher member 108, which functions in the same manner). The locking plate 282 includes an aperture 284 through its thickness. The inner diameter of the aperture 284 is preferably about the same or somewhat greater than an outer diameter of the through-rod 288.

As shown in FIG. 2A, when the long axis of the through-rod 288 is fully or nearly parallel or coaxial with the long axis of the aperture 284, the through-rod 288 can pass freely along its longitudinal axis through the aperture 284 (as indicated by linear motion arrows B), and/or the plate 282 may move freely along a length of the rod 288 (as indicated by linear motion arrows A). However, as shown in FIG. 2B, when the long axis of the aperture 284 is inclined at a sufficient angle relative to the long axis of the through-rod 288 (indicated by rotary motion arrows R), the border of the aperture grips, captures, binds, and/or otherwise engages an exterior surface of the through-rod 288 (e.g., in the regions indicated by designator arrows X), preferably with sufficient force to substantially or completely prevent the through-rod 288 from moving longitudinally relative to the locking plate 282.

In other words, when the aperture 284 is perpendicular to the long axis of the locking plate 282, the through-rod 288 can move freely therethrough when it is perpendicular to the locking plate 282, but will be engaged by the aperture when it is at a non-perpendicular angle relative to the locking plate. In the embodiments described here, the relative angle of a locking plate/keeper member to a through-rod/pusher member is also controlled by a spring-biased angle of the locking plate/ keeper member. Those of skill in the art will appreciate from the figures that such an arrangement will allow free movement in one direction as contact/friction between the through-rod/pusher member and aperture of the locking plate/keeper member in one direction will move them generally perpendicular relative to each other, while movement in the opposite direction will angle them non-perpendicularly and thereby lock them together. Similarly, when the locking plate 282 is functioning as an advancement member (e.g., advancement member 112), the plate 282 may be angled to engage the rod 288 and then pushed in a direction coaxial with the rod's long axis such that the plate 282 will move the rod in the direction the plate is moved.

The external geometry of the through-rod 288 and the aperture 284 do not need to be the same (e.g., the aperture may be—for example—hexagonal, square, or circular, while the cross-sectional geometry of the through-rod may be—for example—elliptical, triangular, or pentagonal). This type of securement is well-known in the art and those of skill in the art will appreciate that various shapes of apertures and/or through-rods may be used within the scope of the present invention, including that the through-rod may be notched or otherwise frictionally-enhanced.

FIG. 1A shows the device 100 in an unactuated state, with the stent 145 being sheathed. Actuation of the device 100 with stent deployment is described with reference to FIG. 1B. To actuate the device 100 and advance the pusher member 108 distally, a user will pivot the lower portion of the trigger 116 toward the handle body 104. This action inclines the advancement member 112 to a first angle where its aperture captures/ engages the pusher member 108 and pushes it forward/distally. During this action, the keeper member 122 is disposed at an angle wherein its aperture 124 allows freely sliding distal-ward passage of the pusher member 108 therethrough. When the trigger 116 is released, the proximal bias of the advancement member 112 moves it back to the default position shown in FIG. 1A. At the same time, the proximal bias of the keeper member 122 generally retains it in the default position shown in FIG. 1A. Serial actuation of the trigger 116 will advance the pusher member 108 and overlying stent 145 distally out of the distal end of the sheath 106 as shown in FIG. 1B.

During deployment of a stent 145 (e.g., into a patient's esophagus), it may be desirable or even needful to reposition the stent longitudinally or otherwise. When the stent 145 has been partially deployed such that it has expanded sufficiently to engage patient tissue, it may be difficult or impossible to move the stent longitudinally and/or rotationally without injuring the patient and/or damaging the stent if it remains expanded. The present device 100 provides for a resheathing function, described with reference to FIG. 1C. As is known in the art, the stent 145 and deployment device 100 may be visualized during a stent-placement procedure by ultrasound and/or fluoroscopy (e.g., based upon the construction of the stent and/or inclusion of specific markers such as echogenic and/or radio-opaque markers included in/on the stent, the device, or any combination thereof). Such visualization, which may also be done using a camera-type device (e.g., optical or electronic endoscope), will enable a physician to monitor and carefully control deployment and—if needed— resheathing/recapture of an expandable prosthesis such as a stent, stent-graft, or other prosthetic device.

If, during deployment, it becomes desirable to partially or completely resheath the stent 145, thereby reducing its outer diameter sufficiently to allow it to be repositioned without damaging the stent or surrounding tissue, a user may actuate (i.e., disengage the brake function of) the keeper member 122 by moving it to an angle generally perpendicular to the pusher member 108, which will release the pusher 108 and allow it to be moved proximally by the user pulling proximally on the loop 138.

In another aspect, the keeper 122 may function as a resheathing trigger. To actuate the keeper 122 in its function as a resheathing trigger and thereby retract the pusher member 108 proximally, a user will pivot the lower portion of the keeper 122 toward the handle body 104 sufficiently to release its engagement with the pusher 108 and then slide the keeper member 122 distally along the pusher 108. When it contacts the handle body 104, the user may then allow the keeper 122 to incline back to a first angle where its aperture captures/engages the pusher member 108 and pulls it (pusher 108) back/proximally (or, more accurately, is pushed back proximally by the bias of the spring 125). Specifically, when the keeper 122 is released, its proximal bias moves it back to the default position shown in FIG. 1A.

The proximal bias of the advancement member 112 by spring 115 generally retains it in the default position shown in FIG. 1A, disposed at an angle wherein its aperture 114 allows freely sliding distal-ward passage of the pusher member 108 therethrough. The device may be constructed such that serial actuation of the keeper 122 will retract the pusher member 108 and overlying stent 145 proximally back into the distal end of the sheath 106 as shown in FIG. 1C, which shows the stent 145 having been partially resheathed. Thereafter, the longitudinal position of the device 100 (with the sheathed stent 145) may be adjusted as desired, and the stent deployed as desired, in the manner described above with reference to FIGS. 1A-1B.

Figure 3A:
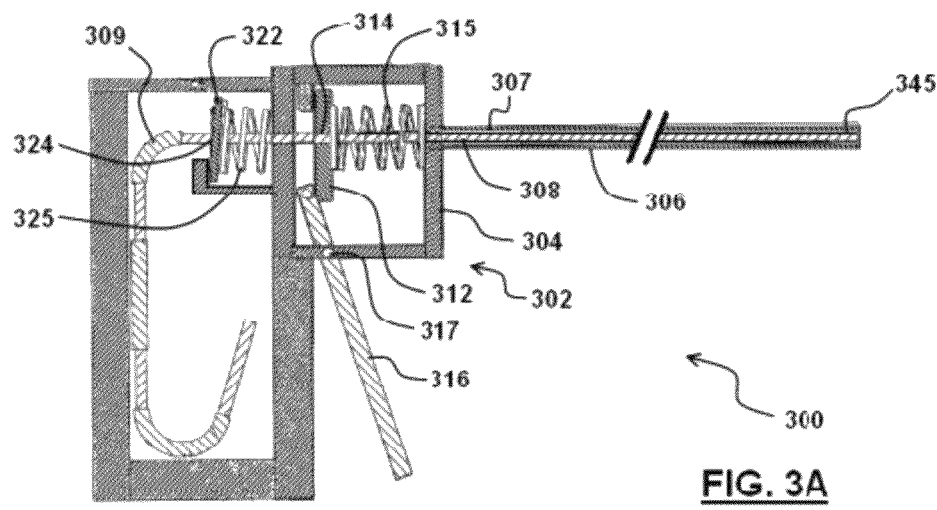
FIGS. 3A-3B show a partial section view of another delivery device embodiment and method of use.
Figure 3B:
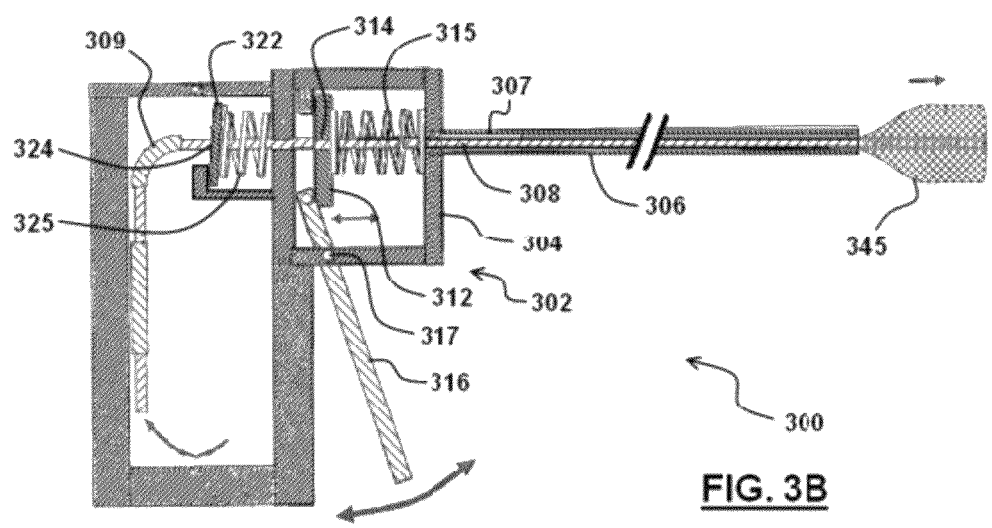

FIGS. 3A-3B show another embodiment of a delivery device 300, with reference to a method of use. The delivery device 300 includes a handle 302 with a handle body 304 and an elongate tubular sheath 306 fixedly attached to and extending distally from the handle body 304. An elongate pusher member 308, including a proximal portion with flexible joint regions 309, extends slidably through a longitudinal lumen 307 of the sheath 306. The flexible joint regions 309 are configured to allow a proximal portion of the pusher member 308 to coil/fold up within the handle body 304. The handle body 304 is shown in a longitudinal section view revealing the internal components of the handle 302.

The interior of the handle 302 includes an advancement member 312 that is biased toward the proximal end of the pusher member 308. In this embodiment, the advancement member 312 is shown as being biased proximally by a coil spring 315, but other biasing means known in the art may be used. The advancement member 312 includes an advancement member aperture 314 through its thickness, through which the pusher member 308 extends. A deployment/advancement trigger member 316 is pivotably mounted to the handle body 304 and is connected to or otherwise disposed in mechanical communication (e.g., operative contact) with the advancement member 312. When the pivot axis 317 is configured as shown, pivoting the lower portion of the trigger member 316 proximally toward the handle body 304 will pivot the upper portion of the trigger member 316 distally, pushing the advancement member 312 distally. When advanced distally by motivation from the deployment trigger member 316, the advancement member 312 engages the pusher member 312 (in the manner described above with reference to FIGS. 2A-2B) and pushes it distally.

A keeper member 322 is mounted within an upper portion of the handle body 304 and biased toward its proximal end against a keeper stop. In this embodiment, the keeper member 322 is shown as being biased by a distally/pulling-tensioned coil spring 325, but other biasing means known in the art may be used. The keeper member 322 includes a keeper member aperture 324 through its thickness, through which the pusher member 308 extends. The keeper member 322 thus is also in mechanical communication with the pusher member 308.

A distal portion of the pusher member 308 is attached to an expandable prosthesis such as, for example, a self-expanding stent 345. The stent 345 may be constrained by this attachment and/or by the sheath 306. A variety of methods and constructions are known and are being developed in the art for providing stent attachment and deployment from a central pusher member whether or not it is accompanied by an outer sheath. Many of these constructions and methods may be practiced in a useful manner within the scope of the present invention, one advantage of which is generally a more compact construction than other devices configured to perform the same or similar functions.

FIG. 3A shows the device 300 in an unactuated state, with the stent 345 being sheathed (and therefore not clearly visible in FIG. 3A). Actuation is described with reference to FIG. 3B. To actuate the device 300 and advance the pusher member 308 distally, a user will pivot the lower portion of the deployment trigger 316 toward the handle body 304. This action inclines the advancement member 312 to a first angle where its aperture captures/engages the pusher member 308 and also pushes it forward/distally. During this action, the keeper member 322 is disposed at an angle wherein its aperture 324 allows freely sliding distal-ward passage of the pusher member 308 therethrough. When the deployment trigger 316 is released, the proximal bias of the advancement member 312 moves it back to the default position shown in FIG. 3A. At the same time, the proximal bias of the keeper member 322 generally retains it in the default position shown in FIG. 3A without retracting the pusher member 308. In this manner, it functions as a "parking brake" preventing undesired motion due to backlash in system components. Serial actuation of the deployment trigger 316 will advance the pusher member 308 and overlying stent 345 distally out of the distal end of the sheath 306 as shown in FIG. 3B.

Figure 4A:
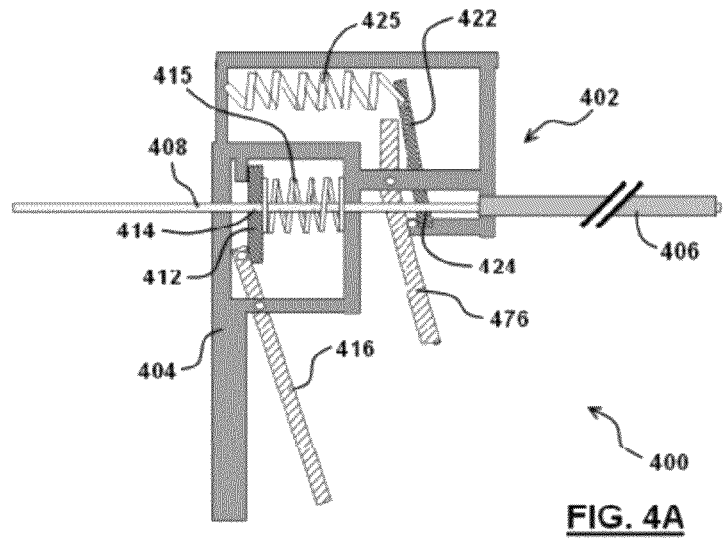
FIGS. 4A-4C show a partial section view of another delivery device embodiment and method of use.
Figure 4B:
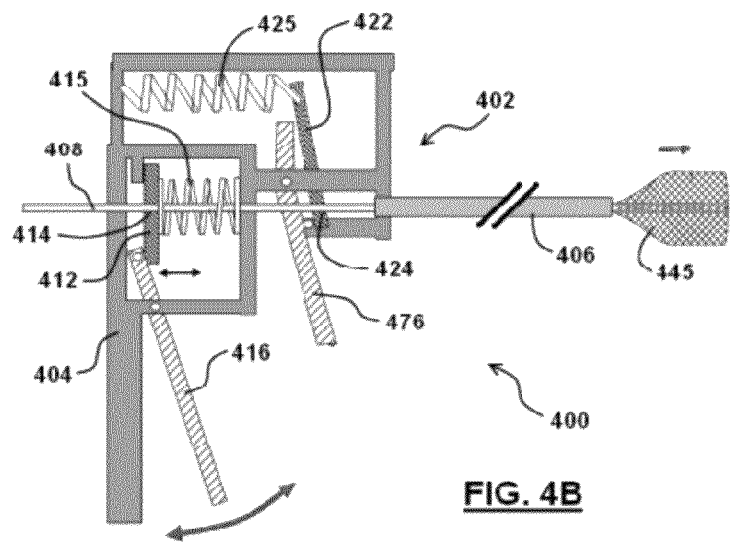
Figure 4C:
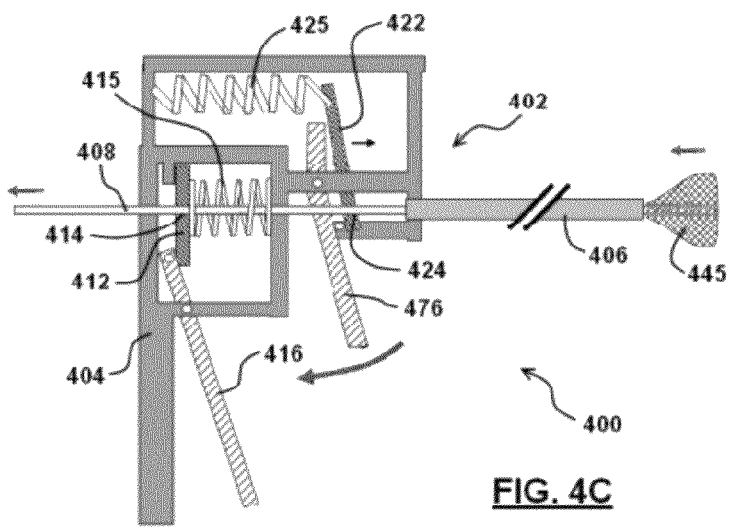

FIGS. 4A-4C show another embodiment of a delivery device 400 that includes a resheathing/brake-release trigger 476, with reference to a method of use. The delivery device 400 includes a handle 402 with a handle body 404 and an elongate tubular sheath 406 fixedly attached to and extending distally from the handle body 404. A pusher member 408 extends slidably through a longitudinal lumen of the sheath 406. The handle body 404 is shown in a longitudinal section view that reveals the internal components of the handle 402.

A first interior portion of the handle 402 includes an advancement member 412 that is biased toward the proximal end of the pusher member 408. In this embodiment, the advancement member 412 is shown as being biased by a coil spring 415, but other biasing means known in the art may be used. The advancement member 412 includes an advancement member aperture 414 through its thickness, through which the pusher member 408 extends. A trigger member 416 is pivotably mounted to the handle body 404 and is connected to or otherwise disposed in mechanical communication with the advancement member 412. When the pivot axis 417 is configured as shown, pivoting the lower portion of the trigger member 416 proximally toward the handle body 404 will pivot the upper portion of the trigger member 416 distally, pushing the advancement member 412 distally. When advanced distally by motivation from the trigger member 416, the advancement member 412 engages (in the manner described above with reference to FIGS. 2A-2B) and pushes distally the pusher member 412.

A keeper member 422 is mounted to and disposed within a second portion of the handle body 404 and is biased toward its proximal end. In this embodiment, the keeper member 422 is shown as being proximally biased by a coil spring 425, but other biasing means known in the art may be used. The keeper member 422 includes a keeper member aperture 424 through its thickness, through which the pusher member 408 extends. A distal portion of the pusher member 408 is attached to an expandable prosthesis such as, for example, a self-expanding stent 445. The stent 445 may be constrained by this attachment and/or by the sheath 406. The keeper member functions as a "parking brake" or retaining means that will prevent backlash movement due to the pusher member 408 and/or sheath member. This may be needed because, as a stent is deployed distally, the sheath 406 may stretch distally and/or the pusher 408 may compress, then—when attempting to relax and return to its original length—it may introduce backlash that would drive the pusher 408 proximally if it weren't held in place. The brake function of the keeper 408 (and of the keeper 108 of FIGS. 1A-1C) will help to mitigate any such backlash.

The trigger 476 and components contacting it are not limited in function to braking/anti-backlash. As will be appreciated with reference to FIGS. 4A-4C, a small degree/distance of actuation will release the braking aspect. In addition, greater actuation (i.e., longer stroke) will move the keeper 422 slidingly along the pusher 408. This will, in turn, build up force in the spring 425, which will—when released—cause the pusher 408 to be moved back proximally in a re-sheathing action (provided that the force provided by the spring is configured to be greater than resistance provided by the stent).

FIG. 4A shows the device 400 in an unactuated state. Actuation is described with reference to FIG. 4B. To actuate the device 400 and advance the pusher member 408 distally, a user will pivot the lower portion of the trigger 416 toward the handle body 404. This action inclines the advancement member 412 to a first angle where its aperture 414 captures/engages the pusher member 408 and pushes it forward/distally. During this action, the keeper member 422 is disposed at an angle wherein its aperture 424 allows freely sliding distal-ward passage of the pusher member 408 therethrough. When the trigger 416 is released, the proximal bias of the advancement member 412 moves it back to the default position shown in FIG. 4A siding along the pusher member 408 without retracting it. At the same time, the proximal bias of the keeper member 422 generally retains the keeper 422 generally in the default position shown in FIG. 4A. Serial actuation of the trigger 416 will advance the pusher member 408 and deploy the overlying stent 445 distally out of the distal end of the sheath 406 as shown in FIG. 4B.

During deployment of a stent 445 (e.g., into a patient's esophagus), it may be desirable or even needful to reposition the stent. When the stent 445 has been partially deployed such that it has expanded sufficiently to engage patient tissue, it may be difficult or impossible to move the stent longitudinally without injuring the patient and/or damaging the stent if it remains expanded. The present device 400 provides for a resheathing function, described with reference to FIG. 4C.

If, during deployment, it becomes desirable to resheath the stent 445, thereby reducing its outer diameter sufficiently to allow it to be repositioned without damaging the stent or surrounding tissue, a user may actuate the keeper member 422 by manually pulling the pusher 408 while operating the second trigger 476 to release the braking function of the keeper 422. To actuate the keeper 422 in a manner that will release and allow proximal retraction of the pusher member 408, a user will pivot the resheathing trigger 476 to angle the keeper 422 (e.g., toward vertical) such that it will allow the pusher 408 to move proximally. Then the user may grasp retract the pusher member 408 and overlying stent 445 proximally back into the distal end of the sheath 406 as shown in FIG. 4C (the stent may be completely resheathed in this and other embodiments even though shown as only partially resheathed here; and, FIG. 4C shows the trigger 476 and keeper 422 back in their default/'braking' position with motion arrows indicating the "release motion" of each). Thereafter, the longitudinal position of the device 400 (with the sheathed stent 445) may be adjusted as desired, and the stent deployed as described above with reference to FIGS. 4A-4B.

The above figures and disclosure are intended to be illustrative and not exhaustive. This description will suggest to one of ordinary skill in the art many variations and alternatives that may be practiced within the scope of the present invention. Those familiar with the art may recognize other equivalents to the specific embodiments described herein which equivalents are also intended to be encompassed by the attached claims. Furthermore, the advantages described above are not necessarily the only advantages of the invention, and it is not necessarily expected that all of the described advantages will be achieved with every embodiment of the invention. The scope of the present invention is defined by the claims directed thereto.

We claim:

1. A controlled release and recapture prosthetic deployment device comprising:
 a handle;
 a tubular sheath fixedly attached to and extending distally from the handle;
 an elongate pusher member extending through the handle and through a longitudinal lumen of the sheath; and
 a self-expanding prosthesis removably disposed within a distal portion of the sheath and attached to the pusher member;
 wherein the handle comprises:
  a handle body;
  an advancement member in the handle body, where the advancement member is biased toward a proximal device end;
  a keeper member attached to the handle body, where the keeper member is also biased toward the proximal device end; and
  a trigger member,
   pivotable relative to the handle body,
   disposed in mechanical communication with the advancement member, and
   configured to move the advancement member distally when the trigger member is pivoted in a first direction;
 wherein the advancement member comprises an advancement member aperture through which the pusher member extends, where the advancement member aperture
  is configured to capturingly engage the pusher member when the advancement member is disposed at a first angle relative to the pusher member, which corresponds with pivoting movement of the trigger in the first direction, and
  is configured to allow freely sliding passage therethrough of the pusher member when the advancement member is disposed at a second angle relative to the pusher member;
 wherein the keeper member comprises a keeper member aperture through which the pusher member extends, where the keeper member aperture is configured to capturingly engage the pusher member to prevent its movement in a proximal direction when the keeper member is disposed at a first angle relative to the pusher member, and is configured to allow freely sliding proximal passage therethrough of the pusher member when the keeper member is disposed at a second angle relative to the pusher member.

2. The device of claim 1, wherein the sheath and the pusher member are flexible and elongate to introduce device the self-expanding prosthesis into a patient's alimentary canal.

3. The device of claim 2, wherein the sheath and the pusher member are flexible and elongate to introduce the self-expanding prosthesis into a patient's esophagus via the patient's mouth.

4. The device of claim 1, wherein the elongate pusher member includes at least one proximal region including at least one flexible joint.

5. The device of claim 4, wherein the at least one flexible joint is configured to allow the at least one proximal region including the at least one flexible joint to coil up within the handle body.

6. The device of claim 4, further comprising a second trigger member attached to the handle body and disposed in mechanical communication with the keeper member and the pusher member.

7. The device of claim 6, wherein the second trigger member mechanical communication with the keeper member and the pusher member is configured such that actuation of the second trigger member engages the keeper member with the pusher member to move the pusher member proximally.

8. The device of claim 7, wherein actuation of the second trigger member moves the self-expanding prosthesis proximally relative to the sheath.

9. The device of claim 1, further comprising a second trigger member attached to the handle body and disposed in mechanical communication with the keeper member and the pusher member.

10. The device of claim 9, wherein the second trigger member mechanical communication with the keeper member and the pusher member is configured such that actuation of the second trigger member engages the keeper member with the pusher member to move the pusher member proximally.

11. The device of claim 10, wherein actuation of the second trigger member moves the self-expanding prosthesis proximally relative to the sheath.

12. A delivery device for delivering a self-expanding prosthesis comprising:
    a handle member;
    a tubular sheath attached to and extending distally from the handle member;
    a first plate member disposed in the handle member and biased toward a proximal end of the handle member, the first plate member including a first aperture therethrough;
    a second plate member disposed in the handle member and biased toward a proximal end of the handle member, the second plate member including a second aperture therethrough;
    an elongate pusher member extending through the first and second apertures and a length of the tubular sheath; and
    a self-expanding prosthesis removably disposed within a distal portion of the sheath and attached to the pusher member;
    wherein the first and second apertures each have a longitudinal axis and are configured such that when said longitudinal axes are disposed in a first orientation, the pusher member will be freely movable in a distal but not a proximal direction, and when said longitudinal axes are disposed in a second orientation, the pusher member will be freely movable in a proximal but not a distal direction.

13. The delivery device of claim 12, configured wherein a distal movement of the pusher member relative to the tubular sheath is configured to deploy the self-expanding prosthesis.

14. The delivery device of claim 12, further comprising a first trigger member disposed in mechanical communication with the first plate member, said mechanical communication configured to, when the trigger is actuated, engage the first aperture with the pusher member and advance the pusher member distally.

15. The delivery device of claim 14, further comprising a second trigger member disposed in mechanical communication with the second plate member, said mechanical communication configured to, when the trigger is actuated, engage the second aperture with the pusher member and move the pusher member proximally.

16. The delivery device of claim 15, wherein the proximal movement is configured to effect a resheathing of any unsheathed portion of the self-expanding prosthesis.

17. A method of deploying a self-expanding prosthesis, said method comprising the steps of:
    providing the delivery device of claim 1; and
    actuating the first trigger to advance the pusher member distally.

18. A method of deploying a self-expanding prosthesis, said method comprising the steps of:
    providing the delivery device of claim 1;
    actuating the first trigger to advance the pusher member distally in a manner unsheathing at least a portion of the self-expanding prosthesis;
    observing a condition making it desirable to at least partially resheath the self-expanding prosthesis; and
    actuating the second trigger and moving the pusher member proximally in a manner at least partially resheathing the self-expanding prosthesis.

* * * * *